United States Patent [19]
Sanagi

[11] Patent Number: 5,152,779
[45] Date of Patent: Oct. 6, 1992

[54] FORCEPS INSTRUMENT

[75] Inventor: Kenichiro Sanagi, Hachioji, Japan

[73] Assignee: Olympus Optical Co., Ltd., Tokyo, Japan

[21] Appl. No.: 530,643

[22] Filed: May 30, 1990

[30] Foreign Application Priority Data

Aug. 11, 1989 [JP] Japan .............................. 1-94776[U]
Mar. 6, 1990 [JP] Japan .............................. 2-22301[U]

[51] Int. Cl.⁵ ...................... A61B 17/28; A61B 17/32
[52] U.S. Cl. ..................................... 606/205; 128/751
[58] Field of Search ............... 606/206, 205, 113, 167, 606/127; 128/751

[56] References Cited

U.S. PATENT DOCUMENTS

| 3,404,677 | 10/1968 | Springer ..................... 606/206 X |
| 4,632,110 | 12/1986 | Sanagi. |
| 4,655,219 | 4/1987 | Petruzzi ............................. 606/206 |
| 4,763,668 | 8/1988 | Macek et al. .................. 606/206 X |

FOREIGN PATENT DOCUMENTS 58-27540 2/1983 Japan.
58-160010 10/1983 Japan.

Primary Examiner—Michael H. Thaler
Attorney, Agent, or Firm—Kenyon & Kenyon

[57] ABSTRACT

An operating portion of an forceps instrument having a slider slidably mounted on an operating body; a holding member divided into two parts for holding an end of an operating wire; and a fixing means for fixing the holding member to the slider. No surplus force is exerted on the holding member during its assembly.

9 Claims, 8 Drawing Sheets

FORCEPS INSTRUMENT

BACKGROUND OF THE INVENTION

1. Field of the Invention

This invention relates to a forceps instrument, such as a biopsy forceps and a grasping forceps, and more particularly to an operating portion of a forceps instrument.

2. Description of Related Art

Figure 1:
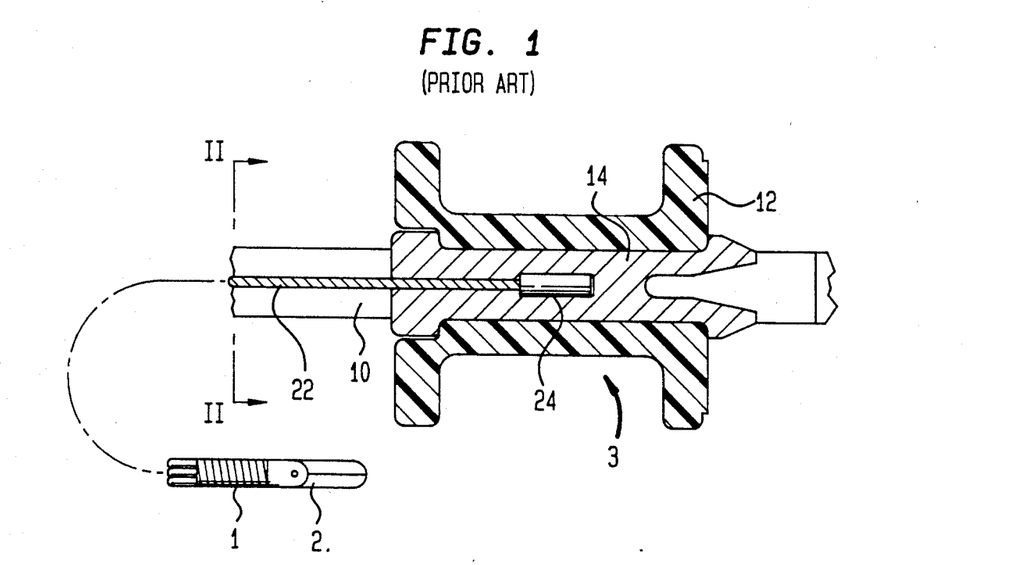
FIG. 1 is a partial sectional view showing an operating portion of a conventional forceps instrument.
Figure 2:
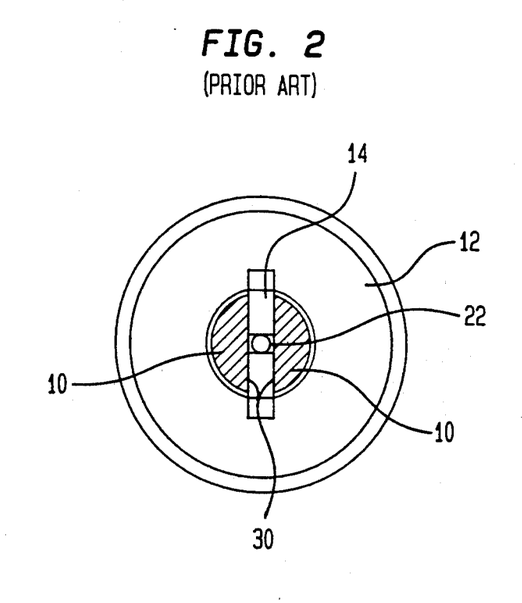
FIG. 2 is a cross-sectional view along line II—II of FIG. 1.
Figure 3:
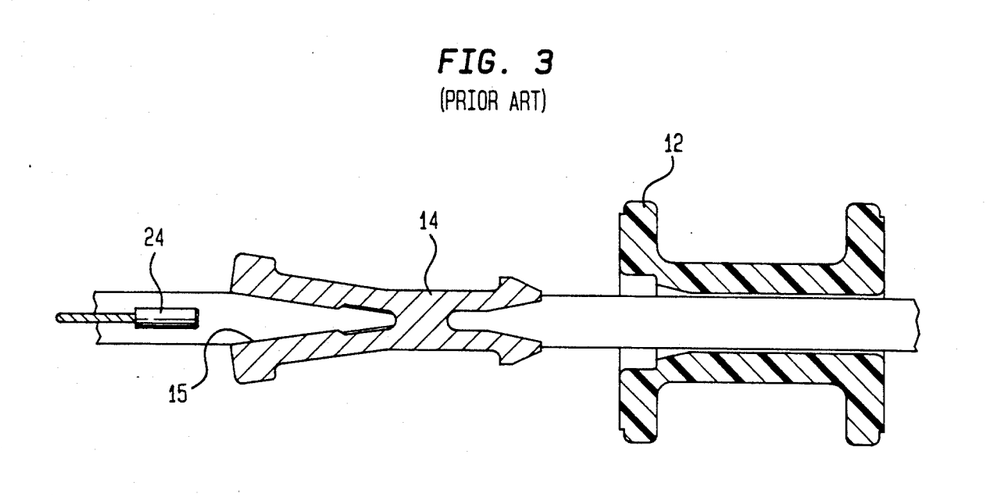
FIG. 3 is a partial sectional view showing the pre-assembly state of the conventional forceps instrument shown in FIG. 1.

As shown in FIGS. 1 and 2, an operating portion 3 of a conventional forceps instrument disclosed in Japanese Laid-Open Utility Model Application, Publication No. 58-160010 includes a flexible sheath 1; an operating wire 22 passing through the flexible sheath 1 for operating a treating portion 2 provided at the distal end of the flexible sheath 1; an operating body 10 provided at the proximal end of the flexible sheath 1; and a slider 12 slidably mounted on the outer periphery of the operating body 10. A holding plate 14 receiving a stopper 24 at the proximal end of the operating wire 22 is inserted into a slit portion 30 of the operating body 10, and the holding plate 14 is fitted into the slider 12 from the state shown in FIG. 3.

In this operating portion 3, in order to prevent the stopper 24 from being drawn out from the holding plate 14, an open portion 15 at the distal end of the holding plate 14 is closed in the slider 12 under a compressive force. Thus, after the operating portion 3 is assembled, the holding plate 14 is always under a radial compressive force. Moreover, when the slider 12 is slided by exerting a force, the force is also exerted on the holding plate 14 so that the holding plate 14 is susceptible to breakage in the vicinity of the bottom of its opening 15. Further, since the holding plate 14 is thinner than the slit portion 30 so as to be inserted into the slit portion 30, the force from the slider 12 will be concentrated on an area without being dispersed, which is also a cause of breakage.

SUMMARY OF THE INVENTION

A main object of the present invention is to provide a forceps instrument with an operating portion which is not broken when a strong force is exerted on its slider.

Another object of the invention is to provide a forceps instrument with an operating portion in which a surplus force is not exerted on a holding member connecting the proximal end of an operating wire to a slider when the operating portion is assembled.

A further object of the invention is to provide a forceps instrument with an operating portion which can be easily assembled and taken apart.

These objects of the invention are attained by a forceps instrument comprising a flexible sheath having a distal end and a proximal end; a treating portion provided at the distal end of the flexible sheath; an operating body provided at the proximal end of the flexible sheath; a slider slidably mounted on the operating body and having an inner surface to form a receiving portion; an operating wire connected at one end thereof to the treating portion and having at the other end thereof a stopper to be connected to the slider whereby the treating portion is operated by advance and retreat movement of the slider; a holding member for holding the stopper of the operating wire, the holding member comprising two parts and having a surface to be fitted in the inner surface of the slider; and fixing means for fixing the holding member to the receiving portion of the slider.

Further, an forceps operating portion according to the present invention comprises an operating body with a slit formed in the axial direction thereof; and a holding member inserted in the slit for holding an end of a wire, the holding member being fixed to a slider without exerting a load on the holding member in a direction perpendicular to the axial direction thereof.

According to the present invention, no surplus force is exerted on the holding member during its assembly, so that the holding member will not be broken even if the slider is moved with a strong force.

DESCRIPTION OF THE PREFERRED EMBODIMENTS

Referring to FIGS. 4 to 8, a forceps instrument of a first embodiment of the present invention is described.

Figure 4:
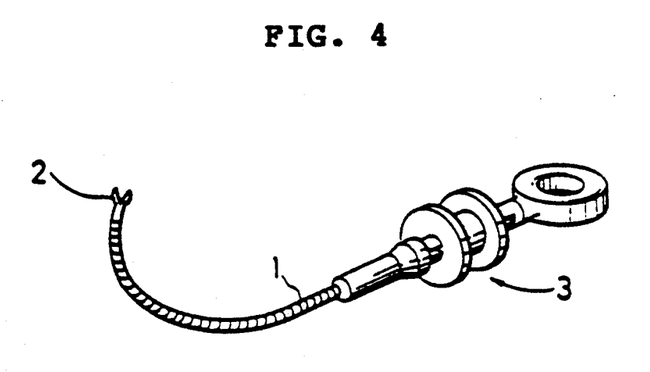
FIG. 4 is a perspective view of a forceps instrument according to a first embodiment of the present invention.

FIG. 4 shows a forceps instrument as a whole. The forceps instrument comprises a flexible sheath 1 formed by a stainless steel coil or a Teflon (trademark) tube; a treating portion 2 at the distal end of the sheath 1; an operating portion 3 at the proximal end of the sheath 1; and an operating wire (not shown) passing through the sheath 1 from the operating portion 3 to the treating portion 2. The movement of the operating portion 3 is transmitted to the treating portion 2 via the operating wire to operate a treating member, such as a biopsy forceps, at the treating portion 2.

Figure 5:
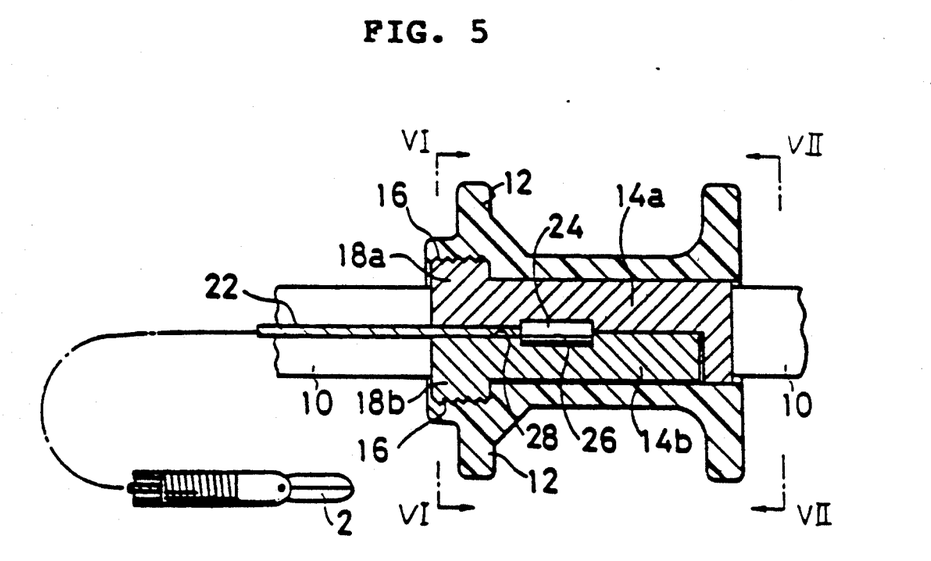
FIG. 5 is a partial sectional view showing an operating portion and a treating portion of the forceps instrument according to the first embodiment.
Figure 6:
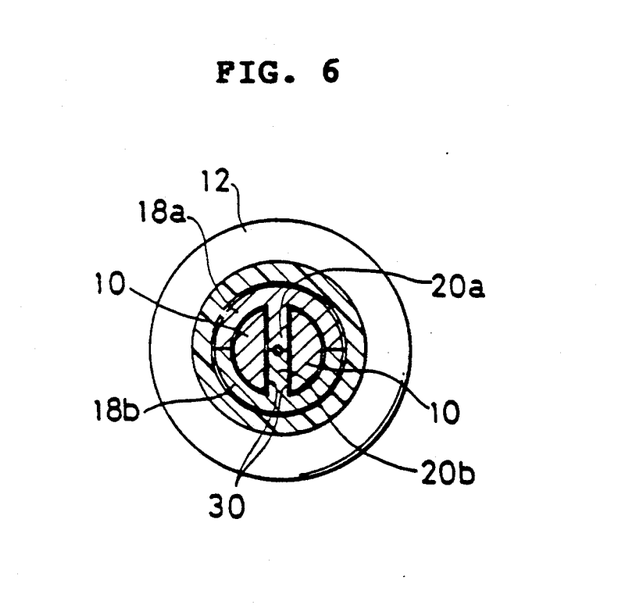
FIG. 6 is a cross-sectional view along line VI—VI of FIG. 5.

FIGS. 5 to 8 show the detail of the operating portion 3 of the forceps instrument shown in FIG. 4. The operating portion 3 mainly includes an operating body 10 at the proximal end of the flexible sheath 1, and a slider 12 slidable along the outer periphery of the operating body 10. A holding member divided into two parts 14a and 14b in its axial direction is inserted between the operating body 10 and the slider 12. The holding member 14a and 14b is formed by semi ring portions 18a and 18b with male threads on their outer peripheries, and a fitting portions 20a and 20b formed integrally with the inner periphery of the semi ring portions 18a and 18b and to be fitted in a slit portion 30 of the operating body 10. The upper and lower semi ring portions 18a and 18b are of the same shape, but the upper and lower fitting portions 20a and 20b are slightly different in the shape of their proximal ends. the upper fitting portion 20a is substantially L-shaped with its tip pointing downward while the proximal end of the lower fitting portion 20b is in the form of an elongated plate. These upper and lower fitting portions 20a and 20b have approximately at their middle position cutout portions 26 for receiving and holding a stopper 24 when both parts 14a and 14b of the holding member are brought into contact with each other as described below. The stopper 24 is provided at the proximal end of the operating wire 22 and has a diameter larger than that of the operating wire 22. Grooves 28 having semicircular cross sections for receiving the operating wire 22 are provided in the boundary surfaces of the upper and lower fitting portions 20a and 20b between the cutout portions 26 and the distal ends of the fitting portions 20a and 20b. The thickness of the fitting portions 20a and 20b is smaller than the width of the slit portion 30 formed in the operating body 10. As shown in FIG. 6, the operating body 10 has semicircular cross sections smaller than the semicircular spaces formed between the parts 14a and 14b of the holding member when the holding member 14a and 14b is assembled to hold the operating wire 22 and the stopper 24, so that the holding member 14a and 14b can be freely moved with respect to the operating body 10.

Figure 7:
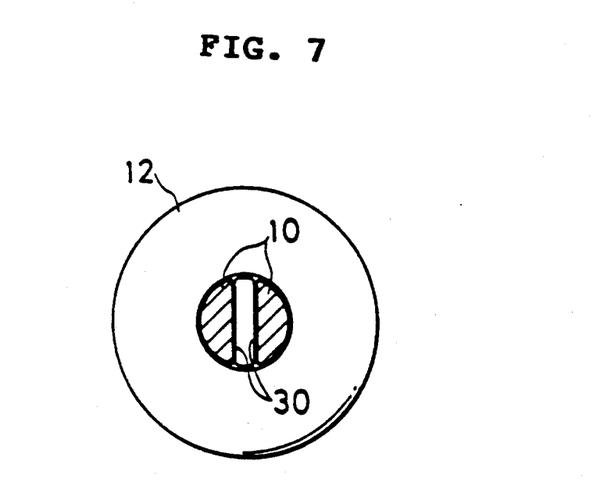
FIG. 7 is a cross-sectional view along line VII—VII of FIG. 5.
Figure 8:
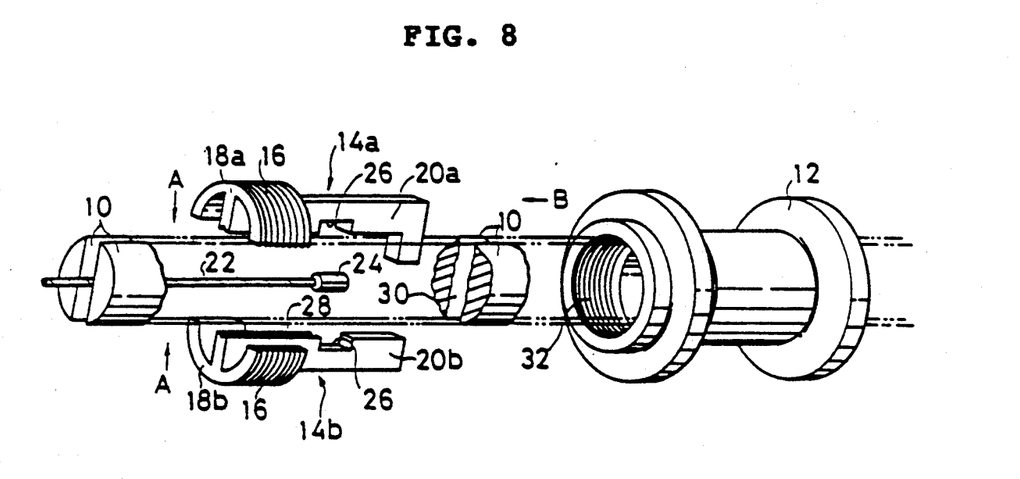
FIG. 8 is a perspective view of the taken-apart operating portion of the forceps instrument according to the first embodiment with certain parts cut off.

The operating portion 3 is assembled in the following manner: The parts 14a and 14b of the holding member are moved from the positions shown in FIG. 8 in the directions shown by the arrows A to hold the operating wire 22 in the grooves 28 and the stopper 24 in the cutout portions 26, and the upper and lower fitting portions 20a and 20b is fitted in the slit portion of the operating body 10. Then, the slider 12 is moved in the direction of the arrow B to engage the male threads 16 provided on the outer periphery of the semi ring portions 18a and 18b of the holding member 14a and 14b with female threads 32 provided on the inner periphery of the distal end of the slider 12. Thus, the assembled operating portion 3 of the forceps instrument shown in FIGS. 5 to 7 is obtained.

Since the slider covers the holding member divided into two parts and sandwiching the operating wire and the operating body, the contacting area of the holding member and the slider is large, thus the holding member will not be broken even if a strong force is exerted on the slider. Further, the holding member is inserted slidably in the slit portion of the operating body and receives no surplus force in a direction perpendicular to the axial direction during the assembly of the operating portion. so that the holding member will not be broken even if the slider is moved with a strong force. Moreover, since the holding member is divided into two parts, the operating portion can be easily assembled and taken apart.

The holding member is formed by either a resin or a plastic.

In the above embodiment, the upper and lower parts 14a and 14b of the holding member has substantially symmetrical shapes with respect to the central axis except for their proximal ends. However, these shapes and the fixing of the holding member and the slider may be varied as described below.

Figure 9:
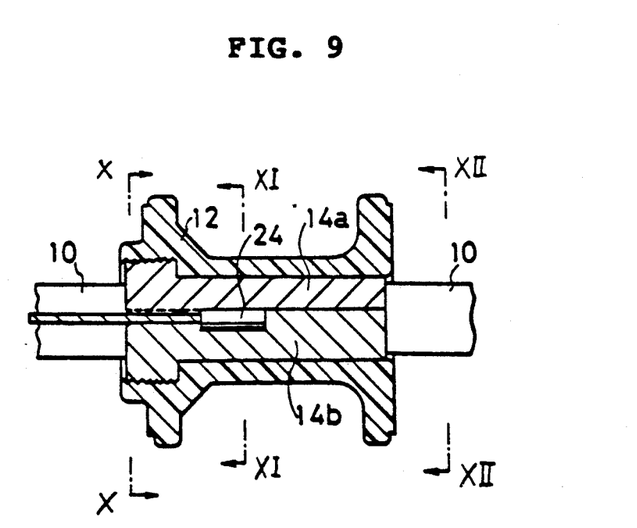
FIG. 9 is a partial sectional view of an operating portion of a forceps instrument according to a second embodiment of the present invention.
Figure 10:
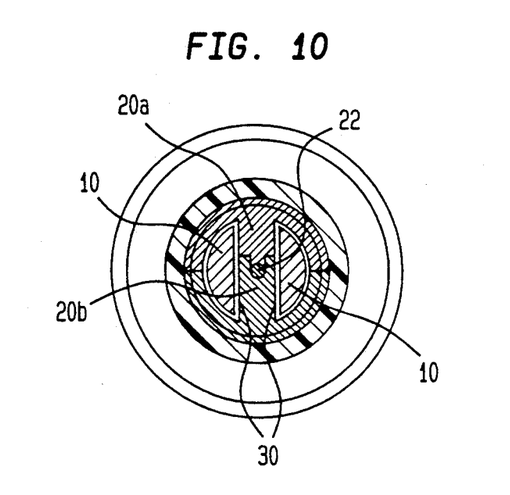
FIG. 10 is a cross-sectional view along line X—X of FIG. 9.
Figure 11:
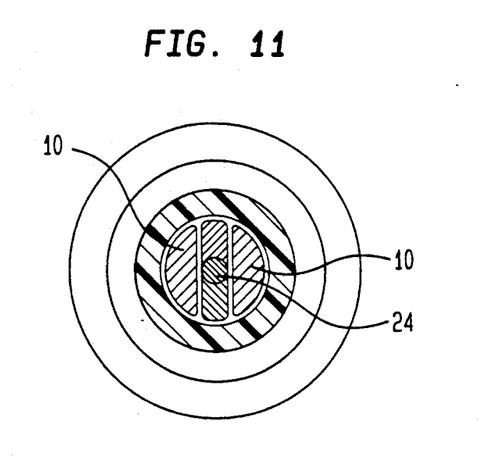
FIG. 11 is a cross-sectional view along line XI—XI of FIG. 9.
Figure 12:
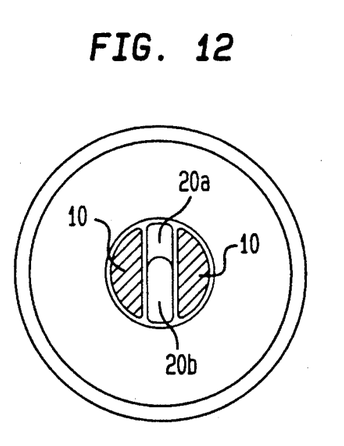
FIG. 12 is a cross-sectional view along line XII—XII of FIG. 9.

FIGS. 9 to 12 show an operating portion of a forceps instrument according to a second embodiment of the present invention. As shown in FIG. 10, an upper fitting portion 20a has a downward protruding portion, and a lower fitting portion 20b has an indented portion, so that an operating wire 22 is held between the upper and lower fitting portions 20a and 20b. As shown in FIGS. 9 and 12, behind a cutout portion 26 for receiving a stopper 24, the upper surface of the lower fitting portion 20b is convex while the lower surface of the upper fitting portion 20a is concave.

Figure 13:
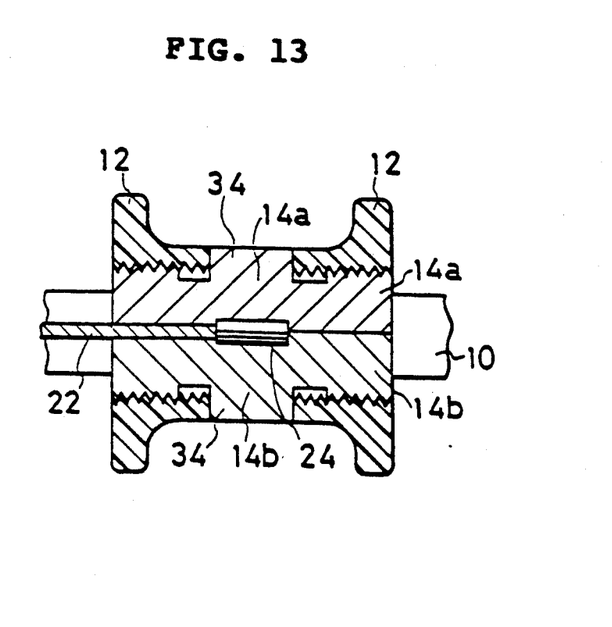
FIG. 13 is a partial sectional view of an operating portion of a forceps instrument according to a third embodiment of the present invention.

FIG. 13 shows a third embodiment of the present invention. A holding member is divided into two upper and lower parts 14a and 14b. When an operating wire 22 and a stopper 24 are sandwiched by these parts 14a and 14b, a circular flange portion 34 is formed in the middle portion. When male threads at both ends of the holding member are engaged with female threads of a slider 12, the outer periphery of the slider 12 is level with the flange portion 34 so that an integral operating portion 3 is assembled.

Figure 14:
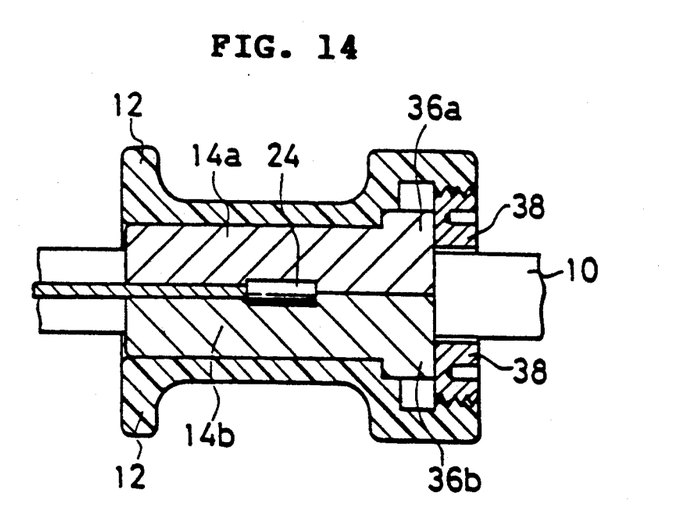
FIG. 14 is a partial sectional view of an operating portion of a forceps instrument according to a fourth embodiment of the present invention.

FIG. 14 shows a fourth embodiment of the present invention in which the fixing method of a holding member 14a and 14b and a slider 12 is changed. In this embodiment, the holding member 14a and 14b is provided at its proximal end with a flange portion 36a and 36b. When male threads on the outer periphery of a ring-shaped collar 38 are engaged with female threads on the inner periphery of the slider 12, the flange portion 36a and 36b is held between the slider 12 and the ring-shaped collar 38 to fix the holding member 14a and 14b to the slider 12.

Figure 15:
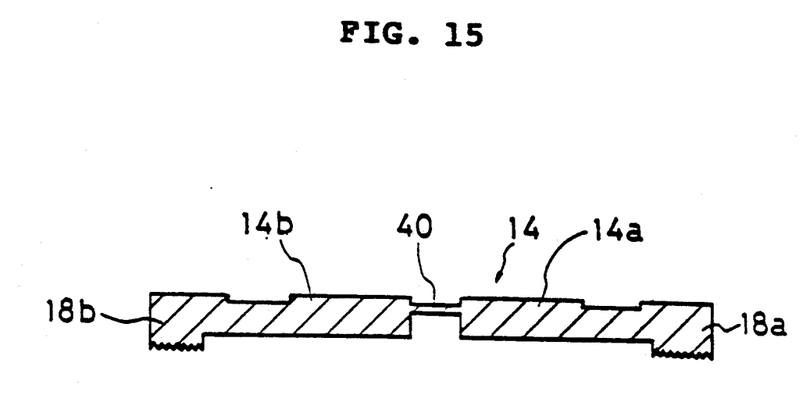
FIG. 15 is a sectional view of a holding member of an operating portion of a forceps instrument according to a fifth embodiment of the present invention.
Figure 16:
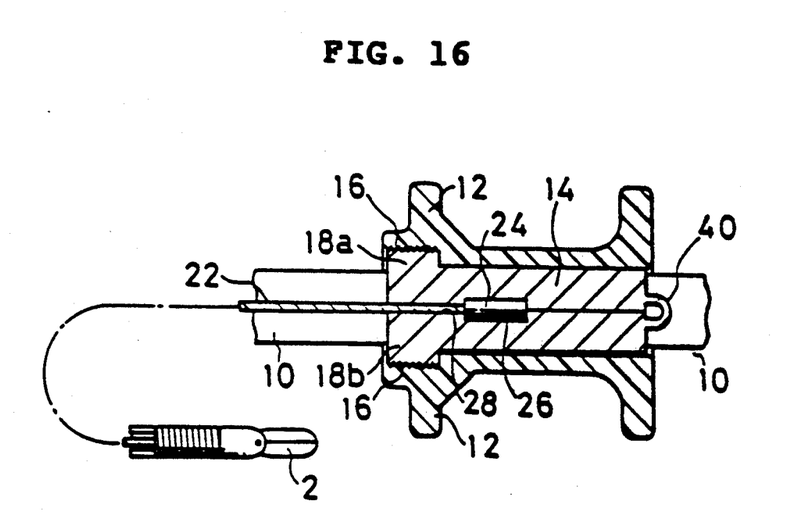
FIG. 16 is a partial sectional view showing the operating portion of the forceps instrument according to the fifth embodiment.

FIGS. 15 and 16 show a fifth embodiment of the present invention in which the holding member of the first embodiment is replaced. As shown in FIG. 15, a holding member 14 is formed by a single member of polysulfone. That is, upper and lower holding portions 14a and 14b are connected by a connecting portion 40. As shown in FIG. 16, the connecting portion 40 is bent to hold a stopper 24 between the upper and lower holding portions 14a and 14b.

The present invention is not limited to the above embodiments, and various changes and modifications may be made in the invention.

What is claimed is:

1. A forceps instrument comprising:
   a flexible sheath having a distal end and a proximal end;
   a treating portion provided at the distal end of the flexible sheath;
   an operating body provided at the proximal end of the flexible sheath;
   a slider slidably mounted on the operating body and having an inner surface to form a receiving portion;

an operating wire having one end and the outer end, the operating wire being connected at the one end to the treating portion and having at the other end a stopper to be connected to the slider whereby the heating portion is operated by advance and retreat movement of the slider;

a holding member formed of a non-metallic material for holding the stopper of the operating wire, the holding member being divided into two separate parts and having a surface to be fitted in the inner surface of the slider, the holding member being provided at one end thereof with male threads to be engaged with the receiving portion by screw connection; and fixing means for fixing the holding member to the receiving portion of the slider, the fixing means engaging the inner surface of the slider with the holding member by screw connection.

2. The forceps instrument of claim 1, wherein the two parts of the holding member have boundary surfaces where the stopper of the operating wire hold, and the holding member is provided in at least one of the boundary surfaces with a path for guiding the operating wire and a cutout portion communication with the path for receiving the stopper of the operating wire.

3. The forceps instrument of claim 1, wherein the operating body is provided with a slit in the axial direction thereof, and the operating wire and the holding member are connected to each other in the slit.

4. The forceps instrument of claim 1, wherein the two separate parts of the holding member each have proximal ends and are connected to each other by a bendable connecting portion at the proximal ends of the parts.

5. A forceps instrument comprising:
a flexible sheath having a distal end and a proximal end;
a treating portion provided at the distal end of the flexible sheath;
an operating body provided at the proximal end of the flexible sheath;
a slider slidably mounted on the operating body and having an inner surface to form a receiving portion;
an operating wire having one end and the other end, the operating wire being connected at the one end to the treating portion and having at the other end a stopper to be connected to the slider whereby the treating portion is operated by advance and retreat movement of the slider, the slider being divided into two parts to form two receiving portions;
a holding member formed of a non-metallic material for holding the stopper of the operating wire, the holding member being divided into two separate parts and having a surface to be fited in the inner surface of the slider, the holding member being provided a both ends thereof with male threads to be engaged with the receiving portions by screw connection; and
fixing means for fixing the holding member to the receiving portion of the slider, the fixing means engaging the inner surface of the slider with the holding member by screw connection.

6. A forceps instrument comprising:
a flexible sheath having a distal end and a proximal end;
a treating portion provided at the distal end of the flexible sheath;
an operating body provided at the proximal end of the flexible sheath;
a slider slidably mounted on the operating body and having an inner surface to form a receiving portion;
an operating wire having one end and the other end, the operating wire being connected at the one end to the treating portion and having a the other end a stopper to be connected to the slider whereby the treating portion is operated by advance and retreat movement of the slider;
a holding member formed of a non-metallic material or holding the stopper of the operating wire, the holding member being divided into two separate parts and having an outer periphery and a surface to be fited in the inner surface of the slider; and
fixing means for fixing the holding member to the receiving portion the slider, the fixing means comprises:
a protruding portion provided on the outer periphery of the holding member;
a contacting surface provided on the inner periphery of the slider for contacting to the protrude portion of the holding member;
female threads provided on the inner surface of the slider; and
a securing member to be engaged with the female threads of the slider by screw connection,
whereby the holding member is fixed to the receiving portion by inserting the holding member into the receiving portion, engaging the securing member with the female threads, and contacting the protruding portion of the holding member to the contacting surface.

7. A forceps instrument comprising:
a flexible sheath having a distal end and a proximal end;
a treating portion provided at the distal end of the flexible sheath;
an operating body provided at the proximal end of the flexible sheath;
a slider slidably mounted on the operating body and having an inner surface to form a receiving portion;
an operating wire having one end and the other end, the operating wire being connected at the eh one end to the treating portion and having tat the other end a stopper to be connected to the slider whereby the treating portion is operated by advance and retreat movement of the slider;
a holding member for holding the stopper of the operating wire, the holding member being provided at one end thereof with male threads to be engaged with the receiving portion by screw connection and comprising:
two parts and having a surface to be fitted in the inner surface of the slider; and
fixing means for fixing the holding member to the receiving potion of the slider, the fixing means engaging the inner surface of the slider with the holding member by screw connection.

8. A forceps instrument comprising:
a flexible sheath having a distal end and a proximal end;
a treating portion provided at the distal end of the flexible sheath;
an operating body provided at the proximal end of the flexible sheath;
a slider slidably mounted on the operating body and having an inner surface to form a receiving portion, the slider being divided into two parts to form tow receiving portions and the holding member being provided at both ends thereof with male threads to be engaged with the receiving portions by screw connection;

an operating wire having one end and the other end, the operating wire being connected at the one end to the treating portion nd having at the other end a stopper to be connected to the slider whereby the treating portion is operated by advance and retreat movement of the slider;

a holding member for holding the stopper of the operating wire, the holding member comprising two parts and having a surface to be fitted in the inner surface of the slider; and fixing means for fixing the holding member to the reeving portion of the slider, the fixing mean engaging the inner surface of the slider with the holding member by screw connection.

9. A forceps instrument comprising:

a flexible sheath having a distal end and a proximal end;

a treating portion provided a the distal end of the flexible sheath;

and operating body provided at the proximal end of the flexible sheath;

a slider slidably mounted on the operating body and having an inner surface to form a receiving portion;

an operating wire having one end and the other end, the operating wire being connected at the one end to the treating portion and having at the other end a stopper to be connected to the slider whereby the heating portion is operated by advance and retreat movement of the slider;

a holding member for holding the stopper of the operating wire, the holding member comprising two parts and having an outer periphery and a surface to be flitted in the inner surface of the slider; and fixing means for fixing the holding member to the receiving portion of of the slider, the fixing means comprises:

a protruding portion provided to the outer periphery of the holding member;

a contacting surface provided on the inner periphery of the slider for contacting to the protruding potion of the holding member;

female threads provided on the inner surface of the slider; and a securing member to be engaged with the female threads of the slider by screw connection, whereby the holding member is fixed to the receiving portion by inserting the holding member into the receiving portion, engaging the securing member with the female threads, and contacting the protruding portion of the holding member to the contacting surface.

* * * * *

UNITED STATES PATENT AND TRADEMARK OFFICE
CERTIFICATE OF CORRECTION

PATENT NO. : 5,152,779

DATED : October 6, 1992

INVENTOR(S) : Kenichiro SANAGI

It is certified that error appears in the above-identified patent and that said Letters Patent is hereby corrected as shown below:

Column 5, line 21, change "wire hold," to --wire is held,--.

Column 5, line 53, change "fited" to --fitted--.

Column 5, line 55, change "a both ends" to --at both ends--.

Column 6, line 10, change "or holding" to --for holding--.

Column 6, line 13, change "fited" to --fitted--.

Column 6, line 15, between "portion" and "the" insert --of--.

Column 6, line 20, change "protrude" to --protruding--

Column 6, line 42, delete "eh".

Column 6, line 43, change "tat" to --at--.

Column 6, line 67, change "tow" to --two--.

Column 7, line 6, change "nd" to --and--.

UNITED STATES PATENT AND TRADEMARK OFFICE
CERTIFICATE OF CORRECTION

PATENT NO. : 5,152,779

DATED : October 6, 1992

INVENTOR(S) : Kenichiro SANAGI

It is certified that error appears in the above-identified patent and that said Letters Patent is hereby corrected as shown below:

Column 7, line 15, change "reeving" to --receiving-- and "mean" to --means--.

Column 7, line 21, change "a the" to --at the--.

Column 7, line 23, change "and operating" to --an operating--.

Column 8, line 3, change "heating portion" to --treating portion--.

Column 8, line 8, change "flitted" to --fitted--.

Column 8, line 13, change "to" to --on--.

Column 8, line 16, change "potion" to --portion--.

Signed and Sealed this

Second Day of November, 1993

*Attest:*

BRUCE LEHMAN

*Attesting Officer*     Commissioner of Patents and Trademarks